(12) United States Patent
Sunvold et al.

(10) Patent No.: US 6,204,291 B1
(45) Date of Patent: Mar. 20, 2001

(54) PROCESS FOR PROMOTING WEIGHT LOSS IN OVERWEIGHT DOGS

(75) Inventors: Gregory Dean Sunvold, Eaton; Mark Alan Tetrick; Gary Mitchell Davenport, both of Dayton, all of OH (US)

(73) Assignee: The Iams Company, Dayton, OH (US)

( * ) Notice: Subject to any disclaimer, the term of this patent is extended or adjusted under 35 U.S.C. 154(b) by 0 days.

(21) Appl. No.: 09/337,938

(22) Filed: Jun. 22, 1999

Related U.S. Application Data (60) Provisional application No. 60/090,882, filed on Jun. 26, 1998.

(51) Int. Cl.$^7$ .................................................. A61K 31/205

(52) U.S. Cl. .............................................................. 514/556

(58) Field of Search .............................................. 514/556

(56) References Cited

U.S. PATENT DOCUMENTS

| | | | |
|---|---|---|---|
| 4,656,191 | 4/1987 | Fanelli | 514/556 |
| 4,883,672 | 11/1989 | Shug et al. | 426/2 |
| 5,030,458 | 7/1991 | Shug et al. | 426/2 |
| 5,192,804 | 3/1993 | Blum et al. | 514/554 |
| 5,540,917 | 7/1996 | Isler et al. | 424/18.01 |
| 5,626,849 | 5/1997 | Hastings et al. | 424/195.1 |
| 5,730,988 | 3/1998 | Womack | 424/195.1 |
| 5,869,528 | 2/1999 | Cavazza | 514/556 |
| 5,895,652 | 4/1999 | Giampapa | 424/195.1 |

FOREIGN PATENT DOCUMENTS

| | | |
|---|---|---|
| 2 735 331 | 12/1996 | (FR) . |
| 03094655 | 4/1991 | (JP) . |
| WO 89/10065 | 11/1989 | (WO) . |
| WO 92/16218 | 10/1992 | (WO) . |

OTHER PUBLICATIONS van Kempen and Odle, "Carnitine Affects Octanoate Oxidation to Carbon Dioxide and Dicarboxylic Acids in Colostrum–Deprived Piglets: In Vivo Analysis of Mechanisms Involved Based on CoA– and Carnitine–Ester Profiles" J. Nutr. 125, 1995, pp. 238–250.

Ji et al., "Atlantic Salmon (*Salmo salar*) Fed L–Carnitine Exhibit Altered Intermediary Metabolism and Reduce Tissue Lipid, but No Change in Growth Rate" J. Nutr. 126, 1996, pp. 1937–1950.

Owen et al., "Effect of L–Carnitine and Soybean Oil on Growth Performance and Body Composition of Early––Weaned Pigs" J. Anim. Sci. 74, 1996, pp. 1612–1619.

Abstract—Sunvold et al., "Effect of dietary carnitine during energy restriction in the canine" FASEB Journal, vol. 13, No. 4, Part 1, 1999, p. A268.

Abstract—L.M. Freeman, "Interventional nutrition for cardiac disease" Seminars in Veterinary Medicine and Surgery (Small Animal), vol. 13, No. 4, 1998, pp. 232–237.

Abstract—Gross et al., "Registration of plasma carnitine levels in dogs and pigs fed suplemental dietary L–carnitine" Journal of Dairy Science, vol. 81, No. Suppl. 1, 1998, p. 186.

Abstract—Gross et al., "Effect of dietary carnitine or chromium on weight loss and body composition of obese dogs" Journal of Dairy Science, vol. 81, No. Suppl. 1, 1998, p. 175.

(List continued on next page.)

Primary Examiner—Phyllis G. Spivack
(74) Attorney, Agent, or Firm—Killworth, Gottman, Hagan & Schaeff, LLP (57) ABSTRACT

A process for feeding a pet food supplement or diet to an overweight canine for the purpose of promoting weight loss, increasing lean body mass, and enhancing the satiety of the animal is provided. The supplement or diet contains an effective amount of L-carnitine.

19 Claims, 7 Drawing Sheets

OTHER PUBLICATIONS

Abstract—Kittleson et al., "Results of the Multicenter Spaniel Trial: Taurine–and carnitine–responsive dilated cardiomyopathy in American Cocker Spaniels with decreased plasma taurine concentrations" Journal of Veterinary Internal Medicine, vol. 11, No. 4, 1997, pp. 204–211.

Abstract—J.K. Gwathmey and A.J. Davidoff, "Pathophysiology of cardiomyopathies: Part II. Drug–induced and other interventions" Current Opinion in Cardiology, vol. 9, No. 3, 1994, pp. 369–378.

Abstract—Grandjean et al., "Dietary supplementation with L–carnitine, vitamin C and vitamin B12 in sport dogs: Experimental study with sledge dogs" Recueil de Medecine Veterinaire de l'Ecole d'Alfort, vol. 169, No. 7, 1993, pp. 543–551.

Abstract—McMillin et al., "Influence of Dietary Fish Oil on Mitochondrial Function and Response to Ischemia" Am. J. Physiol., vol. 263, No. 5 Part 2, 1992, pp. H1479–H1485.

Abstract—Grandjean et al., "Ergogenic Nutritional Supplementation in Efforts of Sporting Dogs" Recl. Med. Vet. Ec. Alfort, vol. 167, No. 7–8, 1991, pp. 753–761.

Abstract—C. Iben, "Effect of L–carnitine in racing sledge dogs" Wiener Tierarztliche Monatsschrift, vol. 85, No. 10, 1998, pp. 334–339.

Abstract—J.K. Goodwin and K.N. Strickland, "The role of dietary modification and nondrug therapy in dogs and cats with congestive heart failure" Veterinary Medicine, vol. 93, No. 10, 1998, pp. 919–926.

Abstract—Chetboul et al., "Use of Isulik (R), an L carnitine supplement, in canine dilated cardiomyopathy" Point Veterinaire, vol. 29, No. 189, 1998, pp. 167–168.

Abstract—D. Grandjean and V. Fuks, "Physiopathological importance of L. carnitine in dogs" Recueil de Medecine Veterinaire, vol. 173, No. 4/5/6, 1997, pp. 95–106.

Abstract—G.J. Jacobs, "Treating cardiomyopathy in dogs and cats" Veterinary Medicine, vol. 91, No. 6, 1996, pp. 544–564.

Abstract—McEntee et al., "Clinical, electrocardiographic, and echocardiographic improvements after L–carnitine supplementation in a cardiomyopathic Labrador" Canine Practice, vol. 20, No. 2, 1995, pp. 12–15.

Abstract—N.D. Costa and R.H. Labuc, "Case report: efficacy of oral carnitine therapy for dilated cardiomyopathy in boxer dogs" Journal of Nutrition, vol. 124, No. 12 Suppl, 1994, pp. 2687S–2692S.

Abstract—Grandjean et al., "Use of a nutritional supplement with L–carnitine, vitamin C and vitamin B12 in sporting dogs. Experimental study in sledge dogs" Recueil de Medecine Veterinaire, vol. 169, No. 7, pp. 543–551.

Abstract—B.W. Keene, "L–carnitine supplement in the therapy of canine dilated cardiomyopathy" Vet Clin North Am Small Anim Pract, vol. 21, No. 6, Sep. 1991, pp. 1005–1009.

Abstract—R.L. Hamlin, "Nutrition and the heart" Vet Clin North Am Small Anim Pract, vol. 19, No. 3, May 1989, pp. 527–538.

Abstract—R.H. Birkhahn and J.R. Border, "Alternate or supplemental energy sources" JPEN J Parenter Enteral Nutr, vol. 5, No. 1, Jan.–Feb. 1981, pp. 24–31.

Abstract—Suzuki et al., "Effects of L–carnitine on ventricular arrhythmias in dogs with acute myocardial ischemia and a supplement of excess free fatty acids" Jpn Circ J, vol. 45, No. 5, May 1981, pp. 552–559.

M.F McCarty: "Promotion of Hepatic Lipid Oxidation and Gluconeogenesis as a Strategy for Appetite Control" Medical Hypotheses, vol. 42, 1994, pp. 215–225.

PROCESS FOR PROMOTING WEIGHT LOSS IN OVERWEIGHT DOGS

CROSS REFERENCE TO RELATED APPLICATION

This patent application claims the benefit of U.S. Provisional Patent Application Ser. No. 60/090,882, filed Jun. 26, 1998.

BACKGROUND OF THE INVENTION

The present invention relates to a process and product for promoting weight loss in overweight dogs, and more particularly to a process for supplementing a canine diet with L-carnitine to promote weight loss, improve body composition, and enhance satiety in the animal.

It is estimated that 20 to 40% of the canine population is overweight or obese. This represents a very large number of animals that are in need of a means to lose weight. Obesity and being overweight are conditions associated with several health risks such as diabetes, increased blood pressure, increased blood triglycerides, impaired locomotion, skeletal stress, increased dystocia, thyroid dysfunction, etc. Consequently, ways to help treat these conditions are much needed by this population of animals. Currently, the most common form of treating obesity in dogs is through the use of diets that contain high amounts of fiber to dilute the calories of the diet.

While in some cases these diets can be effective, they are often associated with several side effects. These include: 1) excessive stool output, 2) decreased nutrient digestibility, 3) poor skin and haircoat, 4) decreased palatability, and 5) constipation and(or) increased frequency of defecation. As a result, alternative nutritional means to alleviate these conditions are needed.

Recently, it has been reported that carnitine, a vitamin-like substance, increased oxidation of octanoate in newborn pigs (van Kempen and Odle, *J. Nutr.* 125:238–250 (1995)), lowered fat deposition and increased fatty acid oxidation by hepatic cells in growing salmon (Ji et al, *J. Nutr.* 126:1937–1950 (19996), and decreased body fat accumulation in growing pigs (Owen et al, *J. Anim. Sci.* 74:1612–1619 (1996).

Accordingly, there is still a need for addressing the obesity problems of canines while still providing adequate nutrition and without the side effects associated with prior diets.

SUMMARY OF THE INVENTION

The present invention addresses the problem of obese and overweight canines through the use of a diet which contains supplemental L-carnitine. L-carnitine is an amino acid co-factor which is synthesized in an animal's body from the amino acids lysine and methionine. We have discovered that L-carnitine, when administered to a canine in need of treatment at extremely low supplemental amounts of 100 mg/kg of diet or less, promotes weight loss in the animal, improves the animal's body composition, and results in enhanced satiety in the animal. By improving the animal's body composition we mean that for a given animal ingesting a given amount of food, the percentage of body fat in the animal will be lower and the percentage of lean body mass will be higher when the animal is provided with the effective amount of supplemental L-carnitine as compared with an animal ingesting the same amount of food, but without L-carnitine supplementation. The L-carnitine may be provided to the animal either as a supplement or contained in a diet fed to the animal. Such a supplement may be in the form of a pill or capsule, a treat or biscuit, or any other edible form. By "diet" we mean the food or drink regularly consumed by the animal.

In accordance with one aspect of the invention, a process for promoting weight loss in canines is provided and includes the step of administering to a canine an effective amount of L-carnitine for a time sufficient to effect a reduction in the weight of the animal. In one embodiment, the L-carnitine may be administered in a diet containing supplemental L-carnitine in an amount of from about 15 to about 195 mg/kg, and preferably from about 25 to about 150 mg/kg of diet. The diet preferably comprises from about 18 to 40 wt % crude protein, about 4 to 30 wt % fat, and about 2 to 20 wt % total dietary fiber, and the L-carnitine is present in the diet in a concentration of between about 15 to about 195 ppm, more preferably about 25 to about 150 ppm, and most preferably about 50 to about 100 ppm.

In another embodiment of the invention, the L-carnitine is administered as a supplement in an amount of from between about 1 to about 100 mg L-carnitine per day, and more preferably from between about 2.5 to about 50 mg L-carnitine per day.

Practice of the present invention is also useful in increasing the lean body mass of a canine as well as enhancing the satiety and decreasing voluntary food intake of a canine.

Accordingly, it is a feature of the invention to provide a process for feeding a pet food supplement or diet for providing weight loss in a canine by providing an effective amount of L-carnitine in the diet of the animal. It is also a feature of the present invention to provide a pet food supplement or diet which increases the lean body mass of the animal. It is also a feature of the present invention to provide a pet food supplement which enhances satiety and reduces voluntary food intake in a canine. These and other features and advantages of the invention will become apparent from the following detailed description, the accompanying drawings, and the appended claims.

DETAILED DESCRIPTION OF THE PREFERRED EMBODIMENT

Dietary supplementation of L-carnitine in amounts of from between about 15 to about 195 ppm, more preferably between about 20 to about 150 ppm, and most preferably about 50 to about 100 ppm, promotes weight loss in overweight canines. Where an effective amount of L-carnitine is fed to dogs that are overweight, this resulted in a greater weight loss than animals fed a diet containing no supplemental L-carnitine. Further, the animals fed an L-carnitine-supplemented diet exhibited a greater percentage of lean body mass(LBM) than animals fed the same diet, but with no L-carnitine supplementation. Also, animals fed an L-carnitine-supplemented diet voluntarily restricted their food intake.

The L-carnitine may be provided in a diet which can comprise any suitable pet food formulation which also provides adequate nutrition for the animal. For example, a typical canine diet for use in the present invention may contain about 1840 wt % crude protein, about 4–30 wt % fat, and about 2–20 wt % total dietary fiber. However, no specific percentages or ratios are required. Preferably, the animal is fed a low-fat L-carnitine-supplemented diet to promote weight loss. A typical low-fat diet may contain about 21.1 wt % protein, about 8.6 wt % fat, and about 1.7 wt % crude fiber. L-carnitine may also be supplied to the canine as a separate dietary supplement such as, for example, in the form of a pill, biscuit, or treat.

In order that the invention may be more readily understood, reference is made to the following example which is intended to illustrate the invention, but not limit the scope thereof.

EXAMPLE

Thirty adult ovariohysterectomized female beagle dogs were used to study the effects of L-carnitine supplementation on weight loss. All of the animals were current on their vaccination and parasite prevention program. The dogs were housed individually in oversize pens and identified by a unique ear tattoo. Fresh water was provided ad libitum during the entire study period. Food intake was adjusted as necessary to achieve the desired weight for the study period.

Three dietary treatments were evaluated. The study consisted of three periods: weight gain, maintenance, and weight loss. During the eleven-week weight gain period, all dogs were fed a single diet Eukanuba Veterinary Diets® Nutritional Recovery Formula™ which contains 36.1 wt % protein, 26.1 wt % fat, and 2.1 wt % crude fiber) ad libitum.

At the initiation of the maintenance phase of the study (baseline or day 0), the dogs were randomized based on body weight into three dietary treatment groups of ten dogs each with a three day feed transition period starting on day 0. Each treatment group was randomly assigned to one of three low-fat diets (Table 1). The only difference between diets was the addition of 0, 50, or 100 ppm supplemental L-carnitine. No differences in the initial body weight or body condition score existed between groups.

TABLE 1

Chemical composition of the low-fat diets

| Nutrient | Amount of Supplemental Carnitine | | |
|---|---|---|---|
|  | 0 ppm | 50 ppm | 100 ppm |
| Protein, % | 20.85 | 21.25 | 21.17 |
| Ash | 5.54 | 5.47 | 5.64 |
| Fat | 8.80 | 8.45 | 8.46 |
| Crude Fiber | 1.55 | 1.63 | 1.82 |

TABLE 1-continued

Chemical composition of the low-fat diets

| Nutrient | Amount of Supplemental Carnitine | | |
|---|---|---|---|
|  | 0 ppm | 50 ppm | 100 ppm |
| Calcium | 0.89 | 0.92 | 0.81 |
| Phosphorus | 0.69 | 0.68 | 0.69 |
| Gross Energy, kcal/g | 4.69 | 4.67 | 4.63 |
| Carnitine, ppm | 21.48 | 73.12 | 126.10 |

The dogs were on 100% experimental diet on day 3 and were fed ad libitum during the seven-week maintenance phase of the study.

During the twelve-week weight loss phase of the study, the same experimental diets were offered as during the maintenance phase. However, the food intake was decreased to produce approximately 1.5 to 2.5% body weight loss per week. Exact amounts of experimental diets were fed to the dogs at approximately the same time each day, and remaining feed amounts were weighed the following day. Food intake and body weight were monitored daily and weekly, respectively. Whole body composition using the Dual Energy X-ray Absorptiometer (DEXA), and blood samples for CBC and chemistry were collected periodically during the study. Whole Body Composition by Dual Energy X-ray Absorptiometry. The dogs were scanned with a Hologic QDR-2000 Plus Dual-Energy X-Ray Absorptiometry (DEXA) bone densitometer, supported with Hologic MXA software, version 8.0. All dogs were anesthetized and placed on the Dual Energy X-ray Absorptiometry (DEXA) table in dorsal recumbency, with legs stretched caudally to avoid overlap of the legs over the body. The dogs were scanned using the Enhanced Array Whole Body software. The body composition measurements recorded consisted of surface area ($cm^2$), bone mineral content (BMC), bone mineral density (BMD), lean mass, fat content, percent fat, and estimated body weight. All measurements were reported in grams except for 2 percent fat and area ($cm^2$). Percent lean and percent BMC were calculated from the lean mass, BMC, and estimated body weight data from the DEXA results.

Anesthesia.

The whole body composition was performed concomitantly and under anesthesia. The anesthetic regimen consisted of Atropine (0.01 mg/lb) as a pre-anesthetic, the combination Xylazine/Telazol/Torbugesic (0.8/6.710.13 mg/kg) as induction and Isoflurane (Aerrane, Ohmeda Pharmaceutical Products, Liberty Corner, N.J.) as a maintenance agent using a nose cone.

Statistical analysis.

A repeated measure classification analysis of variance was used to study "Treatment" and time dependent "Treatment× Time" effects (Gill and Hafs, J. Animal Sci. 33(2):331 (1971)). The variables from the complete blood count, blood chemistry, body composition and body weights were studied using this analysis. All F-tests and mean separations using the Least Square Difference (LSD) used 0.05 Type 1 Error rate. One degree of freedom comparisons between experimental diets B versus C (comparison 1) and A versus B and C (comparison 2) were computed for the body composition and body weight variables. Comparisons 1 and 2 form an orthogonal set. An a of 0.05 was used to test for non-zero value of the mean of the two groups defined per contract. The "Treatment×Time" interaction was investigated by computing a test for linear, quadratic, and cubic response over time for each treatment. Then a test of parallelism, equal quadric response and equal cubic response was done to test equality of trend in response among treatments. An a of 0.05 for the F-tests was used in all cases. All computations were done using SAS (statistical analysis system) software (1989).

Body Weights.

Figure 3:
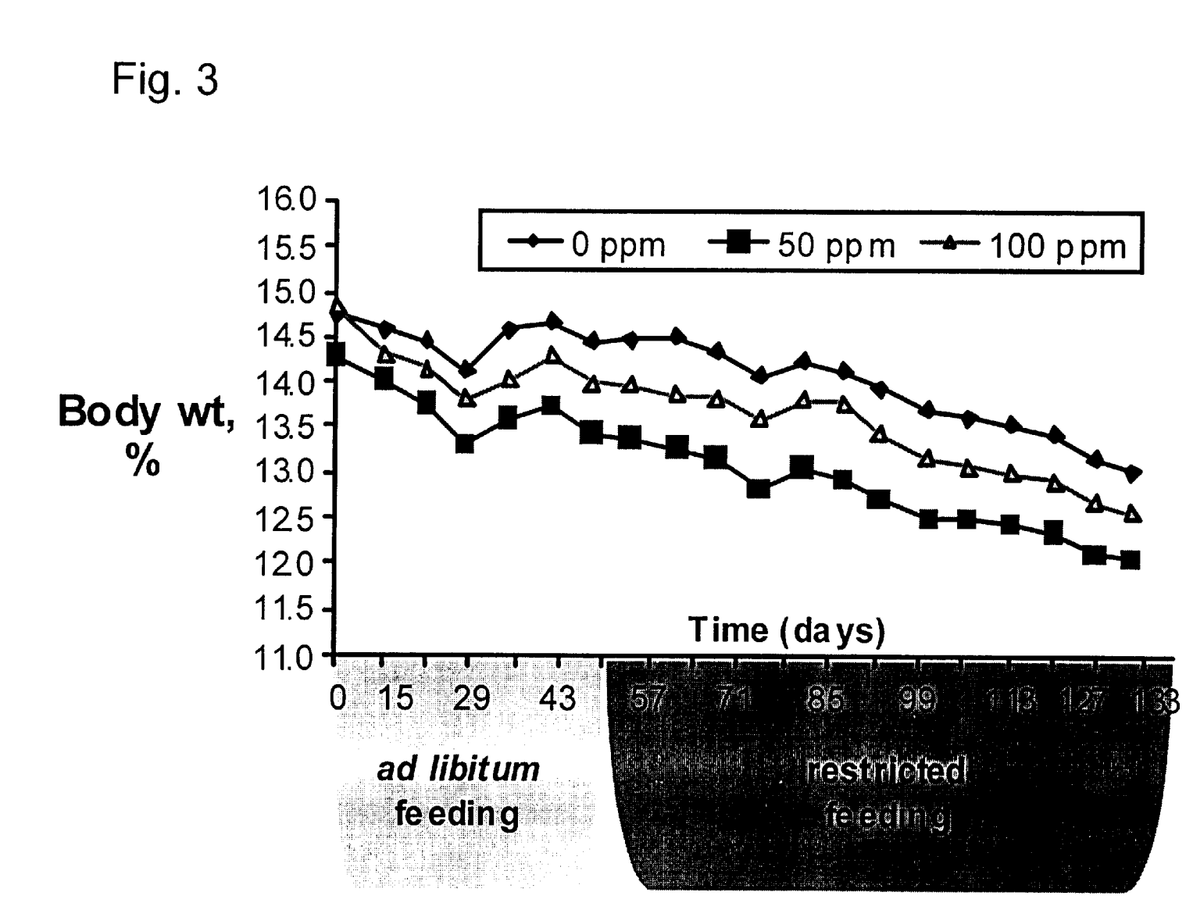
FIG. 3 is a chart illustrating the body weight of dogs during ad libitum and restricted feeding of an L-carnitine supplemented diet.

The animals were randomized based on body weights and subjective body condition scores at the initiation of the maintenance period and the body weights were not different (P>0.05) between treatment groups at that time. The body weight curves remained somewhat parallel during all periods (weight gain, maintenance and weight loss) of the study (See, FIG. 3). During the maintenance and weight loss periods, all groups lost body weight linearly as days progressed. The linear decrease in body weight was greater (P<0.05) for diet B (50 ppm) than diet A (control). The linear decrease of diet C (100 ppm) was intermediate and not different (P>0.05) from either diets A or B. However, the repeated measure analysis revealed that the body weights of all treatment groups were different (P<0.05) at the initiation, mid-point and termination of the weight loss period with treatments A, C, and B having the highest, intermediate, and lowest average body weight, respectively, throughout the study (See, Table 2 below).

Whole Body Composition by DEXA.

The only parameters altered by the test diets were the fat compartment and estimated body weight. All other parameters measured by DEXA were not affected by treatments. The repeated measure analysis revealed that the fat compartment was not different (P>0.05) at the initiation of the study, but all test diets resulted in a very significant (P<0.001) time dependant weight and fat loss as the study progressed. At the initiation and mid-point of the weight loss period, the estimated body weight and fat compartment were different (P<0.05) for all test diets with test diets A, C, and B having the highest, intermediate and lowest averages, respectively. The estimated body weights were also different (P<0.05) at the termination of the weight loss period between the three test diets with the same relationship between test diets as for the mid-point. At the termination of the weight loss period, the fat compartment was significantly larger (P<0.05) for test diet A than for test diets B or C, but test diet B was not different (P>0.05) from test diet C. Table 2 summarizes the body fat means for each time point measured.

TABLE 2

Influence of experimental diets on body fat and weight at baseline (initiation of maintenance period) and during the weight loss period (Means ± STD).

| Diet | Baseline | Initiation Weight Loss* | Mid-Point Weight Loss* | Termination Weight Loss* |
|---|---|---|---|---|
| Fat (grams): | | | | |
| A | 6196 ± 1069 | 5595 ± 994$^a$ | 5246 ± 891$^a$ | 4590 ± 989$^a$ |
| B | 5989 ± 1443 | 4871 ± 1150$^b$ | 4435 ± 932$^b$ | 3772 ± 819$^b$ |
| C | 6201 ± 1344 | 5244 ± 1244$^c$ | 4824 ± 1312$^c$ | 4028 ± 1445$^b$ |
| Body Weight (kg): | | | | |
| A | 14.9 ± 1.8 | 14.5 ± 2.0$^a$ | 13.9 ± 1.7$^a$ | 13.0 ± 1.6$^a$ |
| B | 14.8 ± 2.7 | 13.4 ± 2.1$^b$ | 12.7 ± 1.8$^b$ | 12.1 ± 1.8$^b$ |
| C | 15.0 ± 1.8 | 14.0 ± 1.6$^c$ | 13.4 ± 1.6$^c$ | 12.6 ± 1.6$^c$ |

*Means with different superscript within the same column are statistically significantly different (P < 0.05).

Figure 4:
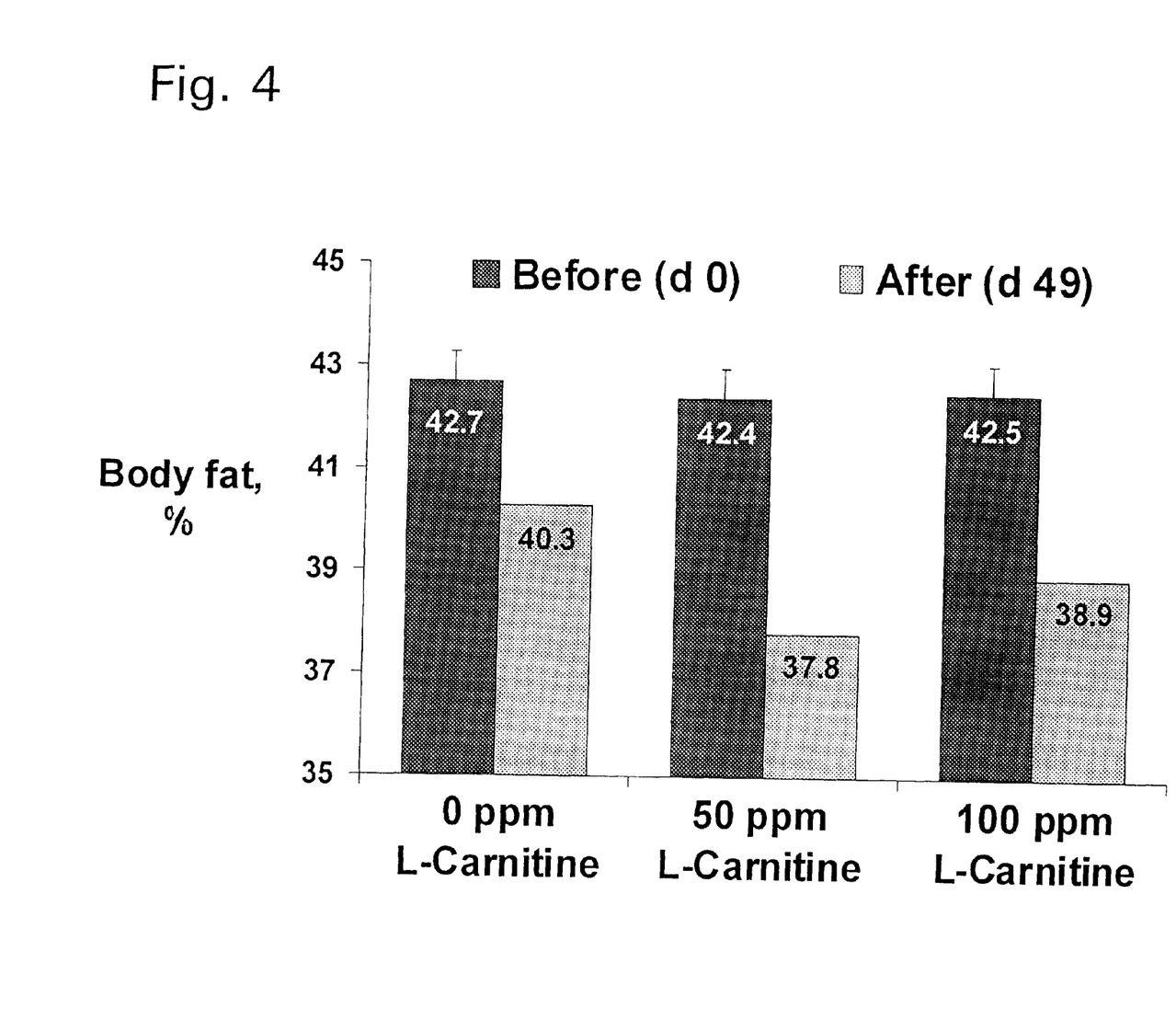
FIG. 4 is a chart illustrating body fat in overweight dogs before and after 49 days of ad libitum feeding of an L-carnitine supplemented diet.

The relative percent change in fat and estimated body weight from baseline revealed a significant difference (P<0.05) between test diet A and test diets B and C (See, FIG. 4). However, test diets B and C were not different (P>0.05) from each other. The relative percent change in BMC from baseline indicated that test diet A lost less (P<0.05) bone mineral content than test diet B. No differences (P>0.05) were noted between test diets A and C or test diets B and C for the relative percent change in BMC.

Hematology and Blood Chemistry.

A time/treatment interaction was detected for the white blood cell (WBC) and the red blood cell (RBC) counts. The WBC tended to decrease as the study progressed for all test diets and the RBC had a more erratic behavior. Nevertheless, these two parameters remained within normal limits for the whole duration of the study. The other hematologic parameters evaluated were not significantly different (P>0.05) between treatments.

A time/treatment interaction was also detected for several blood chemistry parameters, namely glucose, cholesterol, triglycerides, phosphorous, and the enzyme LDH. All test diets resulted in a significant decrease (P<0.05) in blood glucose over time. Although blood glucose levels were different between test diets at several time points, no distinct trend differentiated the effect of one test diet from the others. Test diets B and C tended to decrease the cholesterol levels during treatment but it increased again to meet initial values at the termination of the weight loss study. The cholesterol levels of test diet A was erratic. Although cholesterol levels were different between test diets at several time points, no distinct trend differentiated the effect of one test diet from the others and the cholesterol remained within normal limits during the course of the study. The triglyceride levels increased as the dogs were losing body weight. Test diet B resulted in the highest triglyceride levels (P<0.05) at the end of the study followed by test diet A and then test diet C. The triglyceride levels remained within normal limits throughout the study except for test diet B which exceeded normal limits toward the end of the weight loss period. Although statistical differences were observed for LDH and phosphorous between test diets for several time points, only erratic response patterns were observed for all test diets and the LDH and phosphorous levels remained within normal limits throughout the study.

Figure 1:
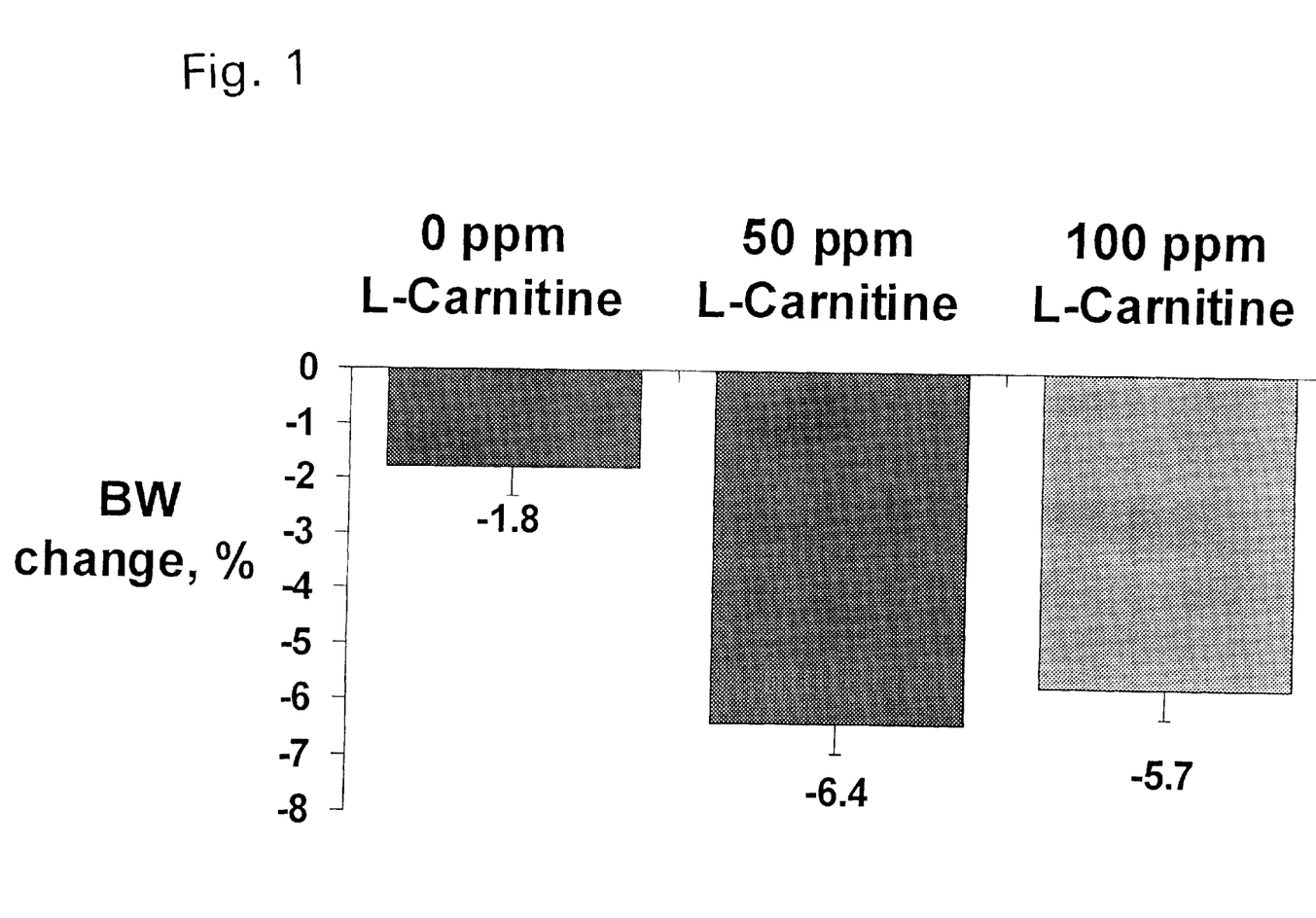
FIG. 1 is a chart illustrating comparative percent body weight change in dogs consuming an L-carnitine supplemented diet versus a non-supplemented diet.

The groups of overweight dogs were fed the respective low-fat diets for seven weeks. As illustrated in FIG. 1, dogs which were fed diets containing supplemental carnitine of 50 and 100 ppm, respectively, achieved a body weight change of −6.4% and −5.7%, respectively, while the control group of dogs (no carnitine supplementation) exhibited only a −1.8% body weight change (P<0.05 from control fed dogs).

Figure 2:
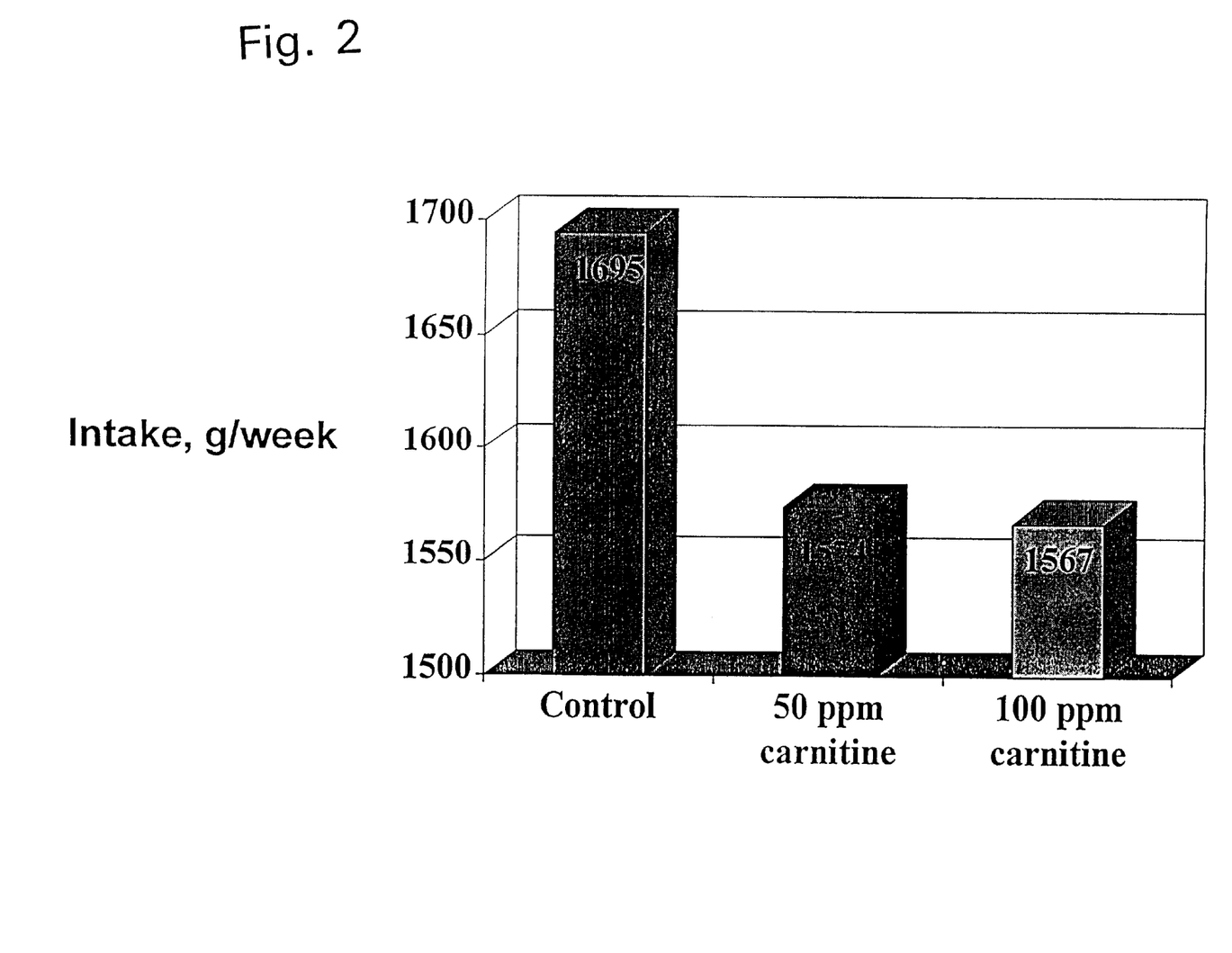
FIG. 2 is a chart illustrating dietary intake in dogs consuming an L-carnitine supplemented diet.

This greater weight loss appeared to occur due to decreased dietary intake. That is, as illustrated in FIG. 2, during seven weeks of feeding, the control group of dogs voluntarily consumed an average of 1695 g/week of the diet, while the carnitine-supplemented groups voluntarily consumed an average weekly amount of only 1574 g/week (50 ppm carnitine) and 1567 g/week (100 ppm carnitine), respectively. Hence, carnitine supplementation promoted satiation as illustrated by the reduced diet intake.

A further benefit of the supplemental carnitine in the dogs' diets was that it promoted an improved body composition of the animals as shown in Table 3 below. As a result of the seven weeks of being fed the experimental diets, lean body mass in the animal (muscle) expressed as a percent of the total body mass was increased for those dogs which were fed the carnitine supplemented diets. As a consequence, fat mass expressed as a percent of the total body mass was decreased with supplemental carnitine.

TABLE 3

Influence of carnitine on body composition in dogs

| Supplemental Carnitine | Body Component | Week 0 | Week 7 |
|---|---|---|---|
| 0 | LBM[a] | 55.7% | 58.2% |
| 50 | LBM | 56.0 | 60.5 |
| 100 | LBM | 55.9 | 59.5 |
| 0 | Fat mass | 42.7 | 40.3 |
| 50 | Fat mass | 42.4 | 37.8 |
| 100 | Fat mass | 42.5 | 38.9 |
| 0 | BMC[b] | 1.5 | 1.5 |
| 50 | BMC | 1.6 | 1.7 |
| 100 | BMC | 1.6 | 1.6 |

[a]LBM = Lean Body Mass
[b]BMC = Bone Mineral Content

The dogs gained an average of 14% body weight and had an average of 42.5% body fat at the end of the weight gain period. The animals lost an average of 15% of their body weight during the maintenance and weight loss phases of the experiment. See, FIGS. 3 and 4. As shown in FIG. 4, 50 and 100 ppm supplemented L-carnitine resulted in more body fat loss ($P<0.05$) compared to 0 ppm supplementation when the difference in body fat between day 0 and day 49 was expressed as a percentage of day 0.

Figure 5:
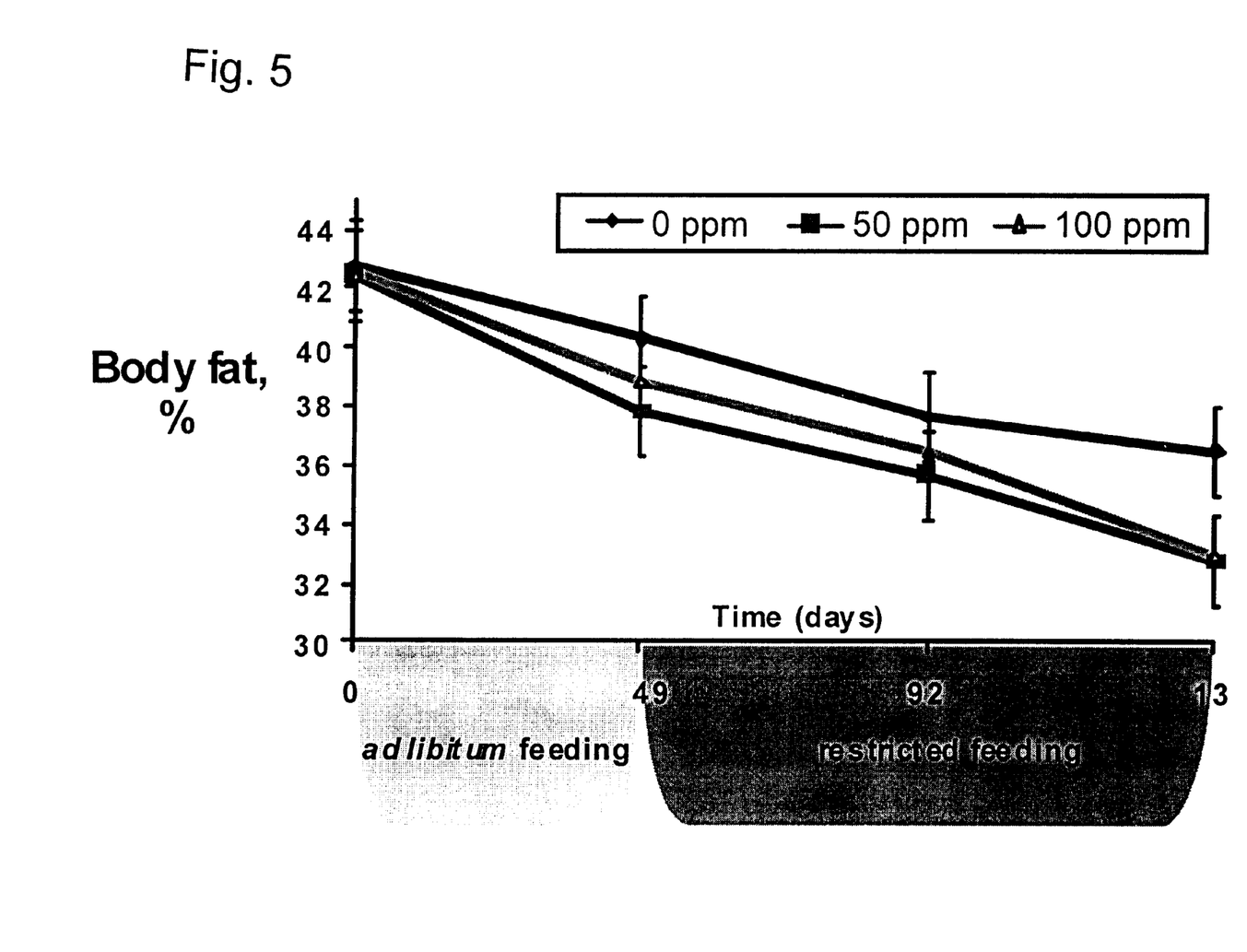
FIG. 5 is a chart illustrating the body fat of dogs during ad libitum and restricted feeding of an L-carnitine supplemented diet.

More fat mass was lost ($P<0.05$) with L-carnitine supplementation. As shown in FIG. 5, 50 and 100 ppm supplemented L-carnitine resulted in more body fat loss ($P<0.05$) compared to no (0 ppm) supplementation when the difference in body fat between day 0 and each subsequent time point (day 49, day 92, and day 133) was expressed as a percentage of day 0.

Figure 6:
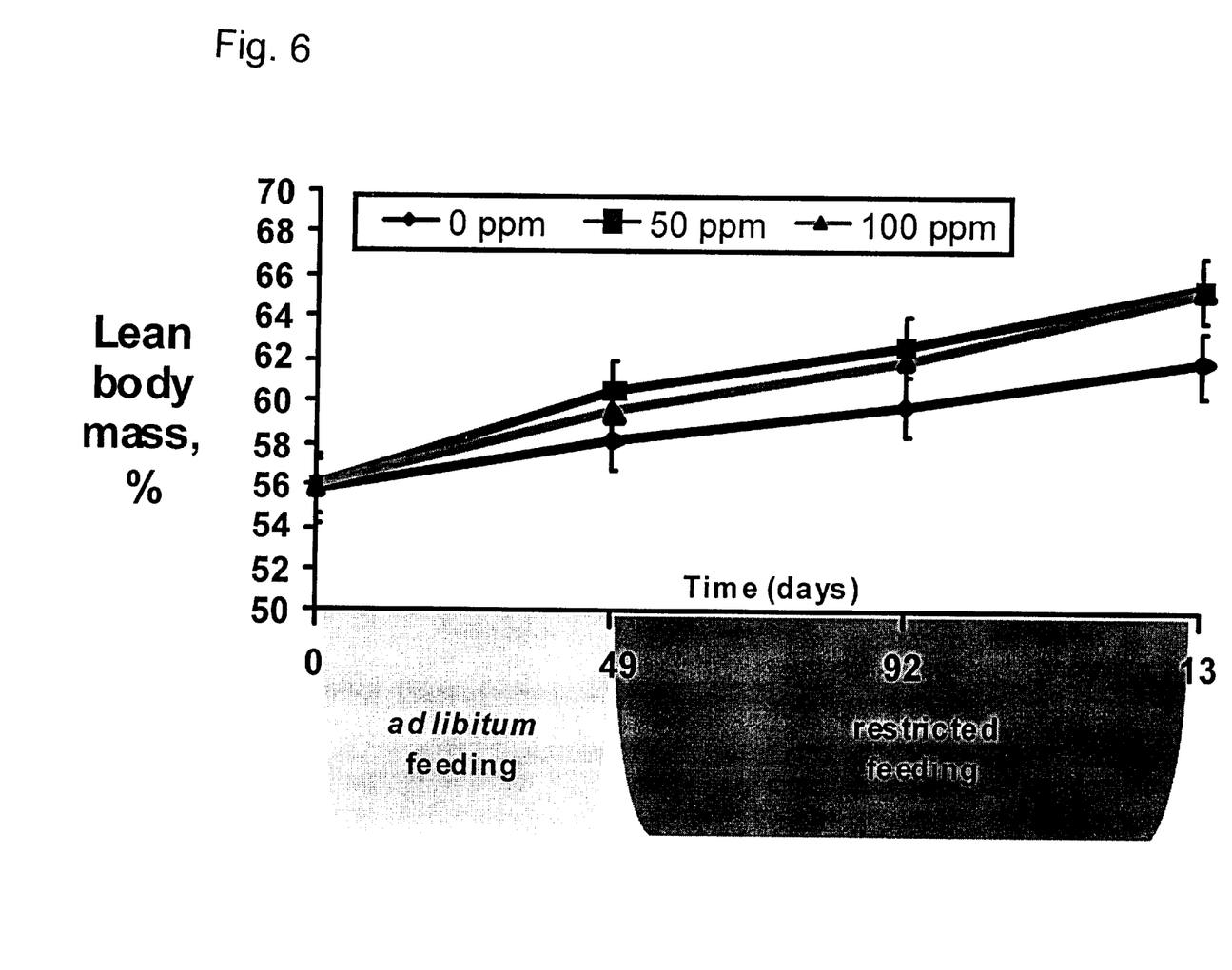
FIG. 6 is a chart illustrating the lean body mass of dogs during ad libitum and restricted feeding of an L-carnitine supplements diet.

Lean body mass of the animals numerically increased with L-carnitine supplementation. As shown in FIG. 6, 50 and 100 ppm supplemented L-carnitine resulted in a leaner body mass for the animals than with no supplementation.

Figure 7:
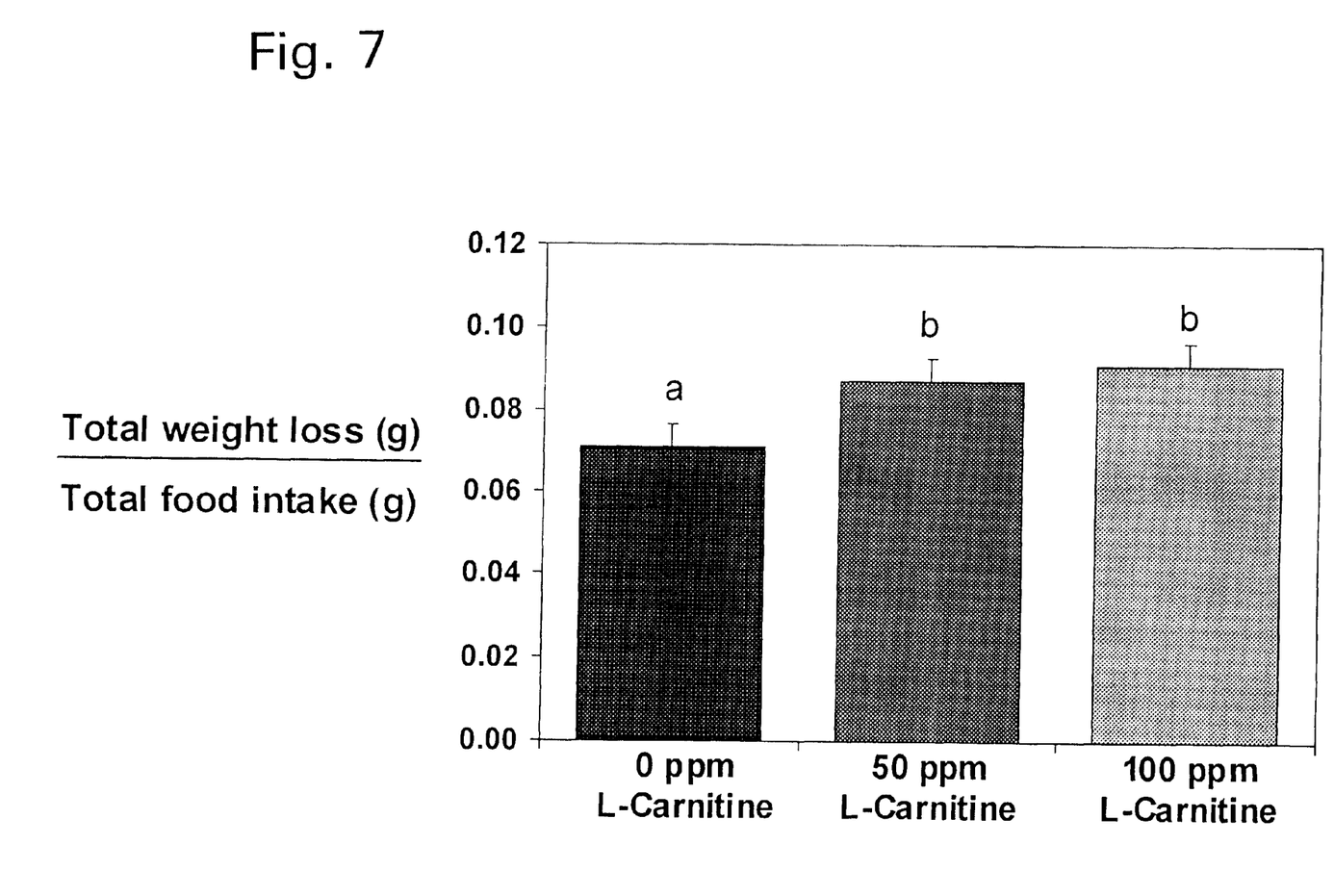
FIG. 7 is a chart illustrating the relationship of weight loss to food intake of dogs during ad libitum and restricted feeding of an L-carnitine supplemented diet.

L-carnitine supplementation resulted in a greater ($P<0.05$) body weight loss per quantity of food consumed. As shown in FIG. 7, 50 and 100 ppm supplemented L-carnitine resulted in a greater total weight loss per total food intake for the animals than with no supplementation.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A process for promoting weight loss in canines comprising the step of administering to a canine a diet containing supplemental L-carnitine in an amount of from about 1 to about 100 mg/kg of diet for a time sufficient to effect a reduction in the weight of the animal.

2. A process as claimed in claim 1 in which said diet comprises from about 18 to 40 wt % crude protein, about 4 to 30 wt % fat, and about 2 to 20 wt % total dietary fiber.

3. A process as claimed in claim 2 in which said diet comprises about 21.1 wt % crude protein, about 8.6 wt % fat, and about 1.7 wt % crude fiber.

4. A process for promoting weight loss in canines comprising the step of administering to a canine a diet consisting of from about 18 to 40 wt % crude protein, about 4 to 30 wt % fat, about 2 to 20 wt % total dietary fiber, and supplemental L-carnitine in an amount of from about 1 to about 100 mg/kg of diet for a time sufficient to effect a reduction in the weight of the animal.

5. A process as claimed in claim 4 in which said diet comprises about 21.1 wt % crude protein, about 8.6 wt % fat, and about 1.7 wt % crude fiber.

6. A process for promoting weight loss in canines comprising the step of administering to a canine a supplement containing L-carnitine in an amount to provide said canine with from about 1 to about 100 mg L-carnitine per day.

7. A process as claimed in claim 6, in which said L-carnitine is administered as a supplement in an amount of from between about 2.5 to about 50 mg L-carnitine per day.

8. A process for increasing the lean body mass of a canine comprising the step of administering to a canine a diet containing supplemental L-carnitine in an amount of from about 1 to about 100 mg/kg of diet for a time sufficient to effect an increase in the lean body mass of said animal.

9. A process as claimed in claim 8 in which said diet comprises from about 18 to 40 wt % crude protein, about 4 to 30 wt % fat, and about 2 to 20 wt % total dietary fiber.

10. A process as claimed in claim 9 in which said diet comprises about 21.1 wt % crude protein, about 8.6 wt % fat, and about 1.7 wt % crude fiber.

11. A process as claimed in claim 8 in which said L-carnitine is present in said diet in a concentration of about 50 to about 100 ppm.

12. A process for increasing the lean body mass of a canine comprising the step of administering to a canine a supplement containing L-carnitine in an amount to provide said canine with from about 1 to about 100 mg L-carnitine per day.

13. A process as claimed in claim 12 in which said L-carnitine is administered as a supplement in an amount of from between about 2.5 to about 50 mg L-carnitine per day.

14. A process for enhancing the satiety and decreasing voluntary food intake of a canine comprising the step of administering to a canine a diet containing supplemental L-carnitine in an amount of from about 1 to about 100 mg/kg of diet for a time sufficient to effect a reduction in the voluntary food intake of the animal.

15. A process as claimed in claim 14 in which said diet comprises from about 18 to 40 wt % crude protein, about 4 to 30 wt % fat, and about 2 to 20 wt % total dietary fiber.

16. A process as claimed in claim 15 in which said diet comprises about 21.1 wt % crude protein, about 8.6 wt % fat, and about 1.7 wt % crude fiber.

17. A process as claimed in claim 14 in which said L-carnitine is present in said diet in a concentration of about 50 to about 100 ppm.

18. A process for enhancing the satiety and decreasing voluntary food intake of a canine comprising the step of administering to a canine a supplement containing L-carnitine in an amount to provide said canine with from about 1 to about 100 mg L-carnitine per day.

19. A process as claimed in claim 18 in which said L-carnitine is administered as a supplement in an amount of from between about 2.5 to about 50 mg L-carnitine per day.

* * * * *